US006132776A

United States Patent [19]
Loeb et al.

[11] Patent Number: 6,132,776
[45] Date of Patent: Oct. 17, 2000

[54] METHODS OF SCREENING FOR NUCLEOSIDE ANALOGS THAT ARE INCORPORATED BY HIV REVERSE TRANSCRIPTASE AND CAUSE INCORRECT BASE PAIRING

[75] Inventors: Lawrence A. Loeb, Bellevue, Wash.; John M. Essigmann, Brookline, Mass.

[73] Assignee: University of Washington, Seattle, Wash.

[21] Appl. No.: 08/876,715

[22] Filed: Jun. 16, 1997

Related U.S. Application Data

[60] Continuation of application No. 08/641,094, Apr. 29, 1996, abandoned, which is a division of application No. 08/268,686, Jun. 29, 1994, Pat. No. 5,512,431.

[51] Int. Cl.[7] .......................... A61K 33/42; A61K 31/70; C07H 21/00
[52] U.S. Cl. ........................... 424/601; 514/43; 536/22.1
[58] Field of Search ................................. 424/601; 435/5, 435/6; 514/43; 536/22.1

[56] References Cited

U.S. PATENT DOCUMENTS

| 5,192,764 | 3/1993 | Cheng et al. | 514/255 |
|---|---|---|---|
| 5,571,666 | 11/1996 | Floyd et al. | 435/2 |
| 5,627,160 | 5/1997 | Lin et al. | 514/49 |
| 5,650,510 | 7/1997 | Webb, II et al. | 544/244 |

OTHER PUBLICATIONS

Shen et al. A comparison of the fidelity of copying 5–methylcytosine and cytosine at a defined DNA template site. Nucleic Acids Research vol. 20)19):5119–5125, Oct. 1992.

Preston et al., "Fidelity of HIV–1 Reverse Transcriptase," *Science* 242 : 1168–1171,1988.

Purmal et al., "Major oxidative products of cytosine, 5–hydroxycytosine and 5–hydroxyuracil, exhibit sequence context–dependent mispairing in vitro," *Nucleic Acids Research* 22 (1):72–78, 1994.

Reardon, J., "Human Immunodeficiency Virus Reverse Transcriptase: Steady–State and PreSteady–State Kinetics of Nucleotide Incorporation," *Biochemistry* 31:4473–4479, 1992.

Ryberg et al., "Human cells contain protein specifically binding to a single $1,N^6$ –ethenoadenine in a DNA fragment," *Proc. Natl. Acad. Sci* . USA 88:6839–6842, 1991.

Shibutani et al., "Insertion of specific bases during DNA synthesis past the oxidation–damaged base 8–oxodG," *Nature* 349: 431–434, 1991.

Singer et al., "Both purified human $1,N^6$ –ethenoadenine–binding protein and purified human 3–methyladenine–DNA glycosylase act on $1,N^6$ –ethenoadenine and 3–methyladenine," *Proc. Natl. Acad. Sci* . USA 89: 9386–9390, 1992.

Wagner et ak,m "Endogenous oxidative damage of deoxycytidine in DNA," *Proc. Natl. Acad. Sci* . USA 89: 3380–3384, 1992.

Wainberg et al., "Characterization of Reverse Transcriptase Activity and Susceptibility to Other Nucleosides of AZT–Resistant Variants of HIV–1. Results from the Canadian AZT Multicentre Study," *Annals of the New York Academy of Sciences* 616: 346–355, 1990.

Wood et al., "Mechanistic Studies of Ionizing Radiation and Oxidative Mutagenesis: Genetic Effects of a Single 8–Hydroxyguanine (7–Hydro–8–oxoguanine) Residue Inserted at a Unique Site in a Viral Genome," *Biochemistry* 29:7024–7032, 1990.

Xu and Swann, "A Simple method for the solid phase synthesis of oligodeoxynucleotides containing $O^4$ –alkylthymine," *Nucleic Acids Research* 18(14):4061–4065, 1990.

Fry and Loeb, "A DNA polymerase αpause site is a hot spot for nucleotide misinsertion," *Proc. Natl. Acad. Sci* . USA 89: 763–767, 1992.

Furman et al., "Phosphorylation of 3'–azido–3'–deoxythymidine and selective interaction of the 5'–triphosphate with human immunodeficiency virus reverse transcriptase," *Proc. Natl. Acad. Sci* . USA 83: 8333–8337, 1996.

Ho and Hitchcock, "Cellular Pharmacology of 2',3'–Dideoxy–2', 3'–Didehydrothymidine, a Nucleoside Analog Active against Human Immunodeficiency Virus," *Antimicrobial Agents and Chemotherapy* 33(6): 844–849, 1989.

Izuta et al., "Inhibitory Effects of Triphosphate Derivatives of Oxetanocin G and related Compounds on Eukaryotic and Viral DNA Polymerases and Human Immunodeficiency Virus Reverse Transcriptase," *Journal of Biochemistry* 112: 81–87, 1992.

Ji and Loeb, "Fidelity of HIV–1 Reverse Transciptase Copying a Hypervarialbe Region of The HIV–1 env Gene," *Virology* 199: 323–330, 1994.

Ji et al., "Mutagenicity and pausing of HIV reverse transcriptase during HIV plus–strand DNA synthesis," *Nucleic Acids Research* 22(1): 47–52, 1994.

Larder and Kemp, "Multiple Mutations in HIV–1 Reverse Transcriptase Confer High–Level Resistance to Zidovudine (AZT)," *Science* 246: 155–1158, 1989.

Michaels et al., "Evidence that MutY and MutM combine to prevent mutations by an oxidatively damaged form of guanine in DNA," *Proc. Natl. Acad. Sci* . USA 89: 7022–7055, 1992.

Nowak, R., "Debate Erupts Over Report of HIV–1 Achilles' Heel," *Journal of NIH Research* 5: 30–31, 1993.

(List continued on next page.)

*Primary Examiner*—John S. Brusca
*Assistant Examiner*—William Sandals
*Attorney, Agent, or Firm*—Seed Intellectual Property Law Group PLLC

[57] ABSTRACT

Methods and compositions related to HIV are disclosed. Using the methods of the present invention, nucleoside analogs may be screened for the ability to be incorporated by reverse transcriptase of human immunodeficiency virus ("HIV RT") and cause incorrect base pairing. Progressive mutation of the virus by such nucleoside analogs renders it non-viable.

6 Claims, 1 Drawing Sheet

OTHER PUBLICATIONS

Prasad et al., "Expression of Enzymatically Active Reverse Transcriptase of Simian Immunodeficiency Virus in Bacteria: Sensitivity to Nucleotide Analogue Inhibitors," *Virology* 179:896–900, 1990.

Baba et al., "Potent and selective inhibition of human immunodeficiency virus type 1 (HIV–1) by 5–ethly–6–phenylthiouracil derivatives through their interaction with the HIV–1 reverse transcriptase," *Proc. Natl. Acad. Sci* . USA 88; 2356–2360, 1991.

Beabealashvilli et al., "Nucleoside 5'–triphosphates modified at sugar residues as substrates for calf thymus terminal deoxynucleotidly transferase and for AMV reverse transcriptase," *Biochimica et Biophysica Acta* 868: 136–144, 1986.

Brent et al., "Repair of O–alkylpyrimidines in mammalian cells: A present consensus," *Proc. Natl. Acad. Sci* . USA 85: 1759–1762, 1988.

Cheng et al., "8–Hydroxyguanine, an Abundant Form of Oxidative DNA Damage, Causes G→ T and A→ C Substitutions," *Journal of Biological Chemistry* 276(1): 166–172, 1992.

Cheng et al., "Human Immunodeficiency Virus Reverse Transcriptase. General Properties and Its Interactions With Nucleoside Triphosphate Analogs," *Journal of Biological Chemistry* 262(5): 2187–2189, 1987.

Cheng et al., "The vinyl chloride DNA derivative $N^2$,3–ethenoguanine produces G→ A transition in *Escherichia coli* ," *Proc. Natl. Acad. Sci* . USA 88: 9974–9978, 1991.

Chung et al., "An endonuclease activity of *Escherichia coli* that specifically removes 8–hydroxyguanine residues from DNA," *Mutation Research* 254: 1–12, 1991.

Dosanjh et al., "Comparative Efficiency of Forming $m^4$ T• G versus $m^4$ T• A Base Pairs at a Unique Site by Use of *Escherichia coli* DNA Polymerase (Klenow Fragment) and *Drosophila melanogaster* Polymerase α–Primase Complex," *Biochemistry* 29: 4698–4703, 1990.

Ellison et al., "Site–specific mutagenesis by $O^6$ –alkylguanines located in the chromosomes of mammalian cells: Influence of the mammalian $O^6$ –alkylguanine–DNA alkyltransferase," *Proc. Natl. Acad. Sci* . USA 86: 8620–8624, 1989.

Feig et al., "Reverse Chemical Mutagenesis: Identification of 5–Hydroxy–2'–Deoxycytidine as a Principal Mutaenic Lesion Caused by Reactive Oxygen Species," *Proceedings of The American Association For Cancer Research* 35: p. 588, Abstract No. 3305, 1994.

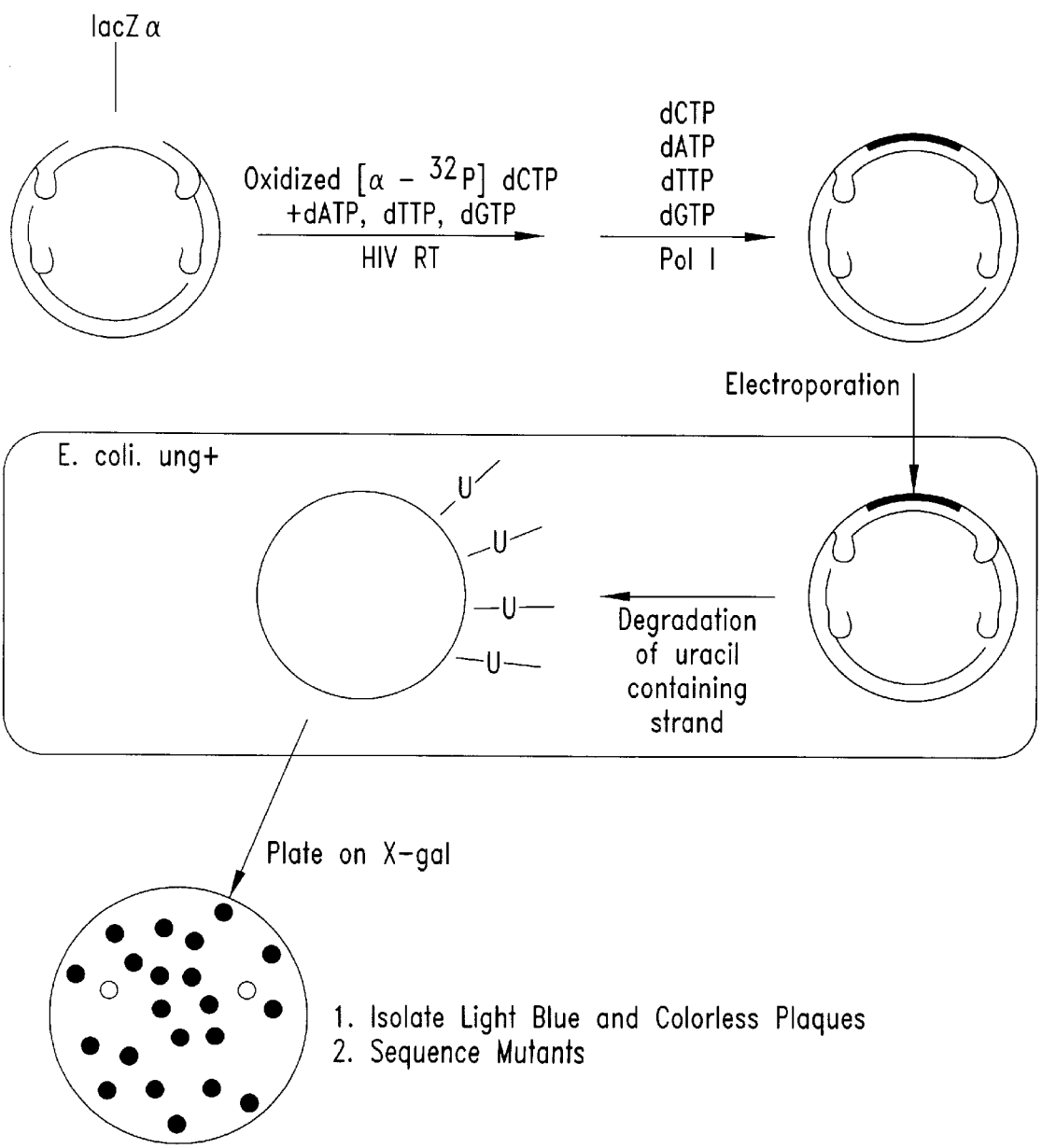

METHODS OF SCREENING FOR NUCLEOSIDE ANALOGS THAT ARE INCORPORATED BY HIV REVERSE TRANSCRIPTASE AND CAUSE INCORRECT BASE PAIRING

CROSS-REFERENCE TO RELATED APPLICATIONS

This application is a continuation of U.S. patent application Ser. No. 08/641,094, filed Apr. 29, 1996, now abandoned; which is a divisional of U.S. patent application Ser. No. 08/268,686, filed Jun. 29, 1994, issued as U.S. Pat. No. 5,512,431.

TECHNICAL FIELD

The present invention is generally directed toward assays for identifying nucleoside analogs for therapy of HIV-infected individuals. This invention is more particularly related to screening candidate nucleoside analogs for the ability to be incorporated and extended by HIV reverse transcriptase and cause incorrect base pairing.

BACKGROUND OF THE INVENTION

Acquired Immune Deficiency Syndrome ("AIDS"), a fatal human disease, is generally considered to be one of the more significant diseases to affect humankind, and has affected numerous individuals worldwide. The disease appears to have originated in Africa and then spread to other locations, such as Europe, Haiti and the United States. AIDS began to be recognized as a distinct new disease in about the mid-1970s. The number of reported cases in the U.S. alone exceeds 100,000. The number of persons in just the U.S. who are infected has been estimated to be greater than one million.

Due to the devastating effect of AIDS on patients and indications that the disease is spreading, much effort has been devoted to elucidate and identify the cause of the disease. Epidemiological data suggested that AIDS is caused by an infectious agent that is transmitted by exposure to blood or blood products. Groups reported to be at greatest risk of contacting AIDS include homosexual or bisexual males and intravenous drug users. Hemophiliacs who receive blood products pooled from donors and recipients of multiple blood transfusions are also at risk.

AIDS is a disease that damages the body's immune system, leaving victims susceptible to opportunistic infections, malignancies or other pathological conditions against which a normal immune system would have protected the subject. After patients develop symptoms of AIDS, death generally occurs within 2–3 years of diagnosis. Clinical manifestations of the disease in its final stage include a collapse of a patient's immune defenses (which generally involves a depletion of helper T cells) accompanied by the appearance of a Kaposi sarcoma and/or various opportunistic infections. The pronounced depression of cellular immunity that occurs in patients with AIDS and the quantitative modifications of subpopulations of their T lymphocytes suggests that T cells or a subset of T cells are a central target for the infectious agent.

The etiology of AIDS and related disorders has been identified as being associated with infection by a new class of lymphotrophic retrovirus termed human immunodeficiency virus (HIV; known previously as HTLV or LAV). It appears that the virus is spread when body fluids, such as semen, vaginal fluids or blood, from an infected individual are passed to an uninfected person. As noted above, AIDS is characterized by a disorder associated with an impaired cell-mediated immunity and lymphopenia, in particular, depletion of those T cells that express the T4 (CD4) glycoprotein. This is due to the fact that HIV preferentially infects the CD4 lymphocyte population (CD4 cells). Both the binding of virus to susceptible target cells and the cell fusion that is a characteristic manifestation of HIV-induced cytopathology involve specific interactions between glycoproteins in the viral envelope and the cell surface of CD4 cells.

HIV contains two heavily glycosylated external envelope proteins, gp120 and gp41, which mediate attachment of virions to glycosylated cell surface receptor molecules. These glycoproteins are encoded by the env gene and translated as a precursor, gp160, which is subsequently cleaved into gp120 and gp41. Gp120 binds to the CD4 protein present on the surface of helper T lymphocytes, macrophages, and other cells, thus determining the tissue selectivity of viral infection.

The CD4 protein is a glycoprotein of approximately 60,000 molecular weight and is expressed on the cell membrane of mature, thymus-derived (T) lymphocytes, and to a lesser extent on cells of the monocyte/macrophage lineage. CD4 cells appear normally to function by providing an activating signal to B cells, by inducing T lymphocytes bearing the reciprocal CD8 marker to become cytotoxic/supressor cells, and/or by interacting with targets bearing major histocompatibility complex (MHC) class II molecules. The CD4 glycoprotein in addition to playing an important role in mediating cellular immunity also serves as the receptor for HIV. A variety of proposed therapeutic approaches have been based upon an attempt to disrupt the interaction of HIV gp120 with T cell CD4.

Once HIV has infected a cell, it replicates to increase the number of copies of the virus. Replication of the HIV genome proceeds by a series of enzymatic reactions involved two virus-encoded enzymes, reverse transcriptase ("HIV RT") and integrase, as well as host cell-encoded DNA polymerases and RNA polymerase. HIV RT polymerizes deoxyribonucleotides by using viral RNA as a template and also acts as a DNA polymerase by using the newly synthesized minus strand DNA as a template to produce a double-stranded DNA. More specifically, HIV RT copies the viral RNA to yield an RNA-DNA hybrid. The RNA strand of the hybrid is degraded and then the viral polymerase copies the resultant single-stranded DNA to yield a double-stranded DNA. The latter is integrated into the host cell genome.

Because of the essential role of HIV RT in the invasion of a host organism by the virus, therapeutic approaches have been based upon an attempt to inhibit HIV RT or to incorporate nucleoside analogs that terminate viral DNA synthesis. The most commonly used drugs against HIV RT are chain terminators. These molecules are presumably incorporated into the polynucleotide chain by HIV RT, but are unable to be extended on subsequent nucleotide additional steps. For example, azidothymidine ("AZT"), one of the most commonly used drugs for the treatment of AIDS, is directed against HIV RT. However, even these inhibitors of HIV RT have been limited success because of the extensive genetic variation and high mutation rate of HIV. Therefore, by rapid evolution of HIV, mutations in HIV RT arise frequently in infected individuals and render the virus resistant to HIV RT inhibitors. This is a significant drawback to conventional therapies.

Although a few drugs such as AZT have prolonged the lives of some individuals with AIDS, there is presently no cure for AIDS. Therapeutic agents are needed for all stages of AIDS infections, to block action of the virus once infection has occurred, and to restore full function in patients whose immune systems have been damaged. Due to the limited success for previously suggested compositions for the treatment of AIDs, there is a need in the art for new therapies and a method to screen for drugs which may be useful in the new therapies. The present invention fills this need, and further provides other related advantages.

SUMMARY OF THE INVENTION

Current methods in the art for the screening of compounds for their effectiveness in the treatment of AIDS are predominantly directed toward the ability to inhibit HIV RT or terminate DNA synthesis following incorporation by HIV RT. Drawbacks of such methods include those summarized above. The method of the present invention are based upon an unconventional approach that exploits, rather than inhibits, HIV RT's ability to incorporate an extend modified nucleotides with high efficiency.

Briefly stated, the present invention provides a variety of methods related to screening nucleoside analogs for the ability to be incorporated by HIV RT and cause incorrect base pairing, and use of such analogs. In one aspect, the present invention provides methods of screening for a nucleoside analog that is incorporated and extended at high efficiency by HIV RT and causes incorrect base pairing. In one embodiment, the method comprises: (a) determining incorporation and extension by HIV RT of a nucleoside analog, and (b) testing the mutagenic potential of the analog.

In another embodiment, the method comprises: (a) testing a plurality of nucleoside analogs for incorporation by HIV RT, (b) purifying the analogs to yield a plurality of purified analogs, (c) determining incorporation and extension by HIV RT of a purified analog, and (d) testing the mutagenic potential of the purified analog.

In another aspect, the present invention provides methods of screening for a nucleoside analog that is incorporated and extended at high efficiency by HIV RT and causes incorrect base pairing, wherein the analog is also incorporated preferentially by HIV RT relative to incorporation by mammalian DNA polymerase. In one embodiment, the method comprises: (a) determining incorporation and extension by HIV RT of a nucleoside analog, (b) testing the mutagenic potential of the analog, (c) determining incorporation by mammalian DNA polymerase of the analog, and (d) comparing the incorporation in steps (a) and (c), therefrom determining whether the analog is incorporated preferentially by HIV RT.

In another embodiment, the method comprises: (a) testing the mutagenic potential of a nucleoside analog, (b) determining extension by HIV RT of the analog, and (c) comparing incorporation by HIV RT of the analog with incorporation by mammalian DNA polymerase, therefrom determining whether the analog is incorporated preferentially by HIV RT.

In another embodiment, the method comprises: (a) testing a plurality of nucleoside analogs for incorporation by HIV RT, (b) purifying the analogs to yield a plurality of purified analogs, (c) determining incorporation and extension by HIV RT of a purified analog, (d) testing the mutagenic potential of the purified analog, (e) determining incorporation by mammalian DNA polymerase of the purified analog, and (f) comparing the incorporation in steps (c) and (e), therefrom determining whether the purified analog is incorporated preferentially by HIV RT.

In another embodiment, the method comprises: (a) testing a plurality of nucleoside analogs for incorporation by HIV RT, (b) purifying the analogs to yield a plurality of purified analogs, (c) testing the mutagenic potential of a purified analog, (d) determining extension by HIV RT of the analog, and (e) comparing incorporation by HIV RT of the purified analog with incorporation by mammalian DNA polymerase, therefrom determining whether the purified analog is incorporated preferentially by HIV RT.

In another aspect, the present invention provides the nucleoside analog, $O^4$-isobutylthymidine. A composition comprises this compound in combination with a pharmaceutically acceptable carrier or diluent.

In another aspect, the present invention provides the isolated nucleoside analog, 5,6-dihydro-5,6-dihydroxydeoxycytidine. A composition comprises this compound in combination with a pharmaceutically acceptable carrier or diluent.

In yet another aspect, the present invention provides methods of treating an individual infected with HIV. In one embodiment, the method comprises administering a therapeutically effective amount of a nucleoside analog, wherein the analog is incorporated and extended at high efficiency by HIV reverse transcriptase and causing incorrect base pairing. In another embodiment, the method comprises administering a therapeutically effective amount of a nucleoside analog, wherein the analog is extended at high efficiency and incorporated preferentially by HIV reverse transcriptase relative to mammalian DNA polymerase and causing incorrect base pairing.

These and other aspects of the present invention will become evident upon reference to the following detailed description and attached drawing.

BRIEF DESCRIPTION OF THE DRAWING

FIG. 1 pictorially depicts the protocol for testing mixtures containing mutagenic nucleoside analogs. The template is a circular M13mp2 DNA containing uracil residues annealed to a linear incomplete complementary strand lacking uracil, so as to crate a 361-nt gap spanning part of the lacZ gene. Incorporation of oxidized dCTP derivatives was done with HIV-RT. The partially double-stranded DNA products were purified, synthesis was completed with the large fragment of E. coli DNA polymerase (Pol I), and the extended product was transferred into E. coli (CSH50). Mutations in lacZ were identified and sequenced, X-gal, 5-bromo-4-chloro-3-indolyl β-D-galactoside.

DETAILED DESCRIPTION OF THE INVENTION

As noted above, the present invention is based upon an unconventional and heretofore unutilized approach that takes advantage of HIV RT's ability to incorporate and extend modified nucleotides with high efficiency. In particular, the present invention, in one aspect, screens for nucleoside analogs that are incorporated and extended at high efficiency by reverse transcriptase of human immunodeficiency virus (hereinafter referred to as "HIV RT"), and cause incorrect base pairing. Such analogs incorrectly base pair at a high frequency, thereby increasing the mutational rate of HIV. Mutations are induced throughout the viral genome, including at those sites that are essential for viability. Once the mutational threshold for viability is exceeded, the probability for producing viable viral progeny is progressively smaller with each round of viral replication. The end result is non-viable mutant viral genomes. Therefore, the nucleoside analogs, rather than inhibiting HIV RT or incorporating only once and terminating DNA synthesis, are extended by HIV RT but are lethally mutagenic for HIV.

Nucleoside analogs suitable within the present invention are those that are incorporated and extended at high efficiency by HIV RT and cause incorrect base pairing. As used herein, the term "nucleoside analogs" include analogs of nucleosides and the triphosphates thereof. Examples of such compounds include 8-hydroxydeoxyguanosine; $O^6$-methyldeoxyguanosine; $O^6$-ethyldeoxyguanosine; $O^6$-isopropyldeoxyguanosine; $O^6$-isobutyldeoxyguanosine; 5-hydroxymethyldeoxycytidine; $O^4$-methylthymidine; $O^4$-ethylthymidine; $O^4$-isopropylthymidine; 3,$N^4$-ethenodeoxycytidine; 3,$N^2$-ethenodeoxyguanosine; 1,$N^6$-ethenodeoxyadenosine; 8-aminodeoxyguanosine; 5-hydroxydeoxycytidine; and 5,6-dihydro-5,6-dihydroxydeoxycytidine.

Briefly, 8-hydroxydeoxyguanosine is prepared according to a combination of the procedures of Bodepudi et al. (*Chem. Res. Tox.* 5:608–617, 1992) and Lin et al. (*J. Med. Chem.* 28:1194–1198, 1985) using commercially available 2'-deoxyguanosine as the starting material. $O^6$-Methyldeoxyguanosine, $O^6$-ethyldeoxyguanosine and $O^6$-isopropyldeoxyguanosine are prepared according to the procedure of Fathi et al. (*Tetrahedron Lett.* 3:319–322, 1990) using commercially available 2'-deoxyguanosine as the starting material. 5-Hydroxymethyldeoxycytidine is prepared based upon the procedure of Itahara et al. (*Chem. Lett.* 1591–1594, 1991) using commercially available 5-methyl-2'-deoxycytidine as the starting material. $O^4$-Methylthymidine, $O^4$-ethylthimidine and $O^4$-isopropylthymidine are prepared according to the procedure of Xu et al. (*Nuceleic Acids Res.* 18:4061–4065, 1990) using commercially available thymidine as the starting material. 3,$N^4$-Ethenodeoxycytidine is prepared according to the procedure of Eberle et al. (*Carcinotenesis* 10:2751–2756, 1989) using commercially available 2'-deoxycytidine as the starting material. 3,$N^2$-Ethenodeoxyguanosine is prepared according to the procedure of Kusmierek et al. (*Chem. Res. Toxicol.* 5:634–638, 1992) using commercially available 2'-deoxyguanosine as the starting material. 1,$N^6$-Ethenodeoxyadenosine is commercial available. 8-Aminodeoxyguanosine is prepared according to the procedure of Long et al. (*J. Org. Chem.* 32:2751–2756, 1967) using commercially available 2'-deoxyguanosine as the starting material. 5-Hydroxydeoxycytidine is prepared based upon the procedure of Eaton et al. (*Biochem. Biophy. Acta* 319:281–287, 1973) using commercially available 2'-deoxycytidine as the starting material. 5,6-Dihydro-5,6-dihyroxydeoxycytidine is prepared based upon the procedure of Basu et al. (*Proc. Natl. Acad. Sci. USA* 86:7677–7681, 1989) using commercially available thymidine as the starting material.

In addition, derivatives possessing the appropriate properties (i.e., ability to be incorporated and extended at high efficiency by HIV RT and to cause incorrect base pairing) are also suitable within the present invention. Examples of derivatives include the replacement of a methyl or ethyl group with a butyl group. $O^4$-isobutylthymidine is an example of such a derivative. This compound is prepared based on the procedure of Xu et al. (*Nucleic Acids Res.* 18:4061–4065, 1990) for $O^4$-methylthymidine, except replacing methanol with isobutyl alcohol.

The phosylation of deoxynucleoside analogs to the level of triphosphates is carried out by a combination of enzymatic phosphorylation to the monophosphate level using the phosphoryltransferase reaction and then by chemical conversion of the monophosphates to form the 5'-triphosphates. Enzymatic phosphorylation is carried out using the crude wheat shoot extract as a source of phosphotransferase activity (Giziewicz and Shugar, *Acta Biocim. Pol.* 22:87–98, 1975; Sugar, *In Molecular Aspects of Chemotherapy*, Springler-Verlag, 1991, pp. 240–270). For example, this approach has been used for the phosphorylation of $O^2$-alkylthymidines by Singer (*Biochemistry* 28:1478–1483). Human peripheral red blood cell lyzates can be used as an alternative source of phosphotransferase activity. Alternatively, phosphorylation can be carried out by Herpes virus thymidine kinase or mutants derived thereof as described by Black and Loeb (*Biochemistry* 32:11618–11626, 1993). Herpes thymidine kinase has a wide substrate specificity and phosphorylates a variety of nucleoside analogs. The resultant deoxynucleoside monophosphates are purified by high pressure liquid chromatography.

The conversion of the 5'-deoxynucleoside monophosphate analogs to the 5'-triphosphate is by the procedure of Hoard and Ott (*J. Am. Chem. Soc.* 87:1785–1788, 1965). To a solution of 0.1 mmol of the deoxynucleoside 5'-monophosphate as an anhydrous tributylammonium salt in 2 ml of dimethylformamide is added 0.5 mmol of 1,1'-carbonyldiimidazole. The mixture is incubated for 4 hours at 24° C. and then treated with 0.8 mmol of methanol. Tributylammonium pyrophosphate (0.5 mmol) in 5 ml of DMF is added and the precipitated imidazolium pyrophosphate is removed by centrifugation. The supernatant is treated with an equal volume of methanol, evaporated to dryness, chromatographed on DEAE-cellulose, and eluted by a gradient of triethylammonium bicarbonate at pH 7.5. Triethylammonium bicarbonate is removed from the product of the reaction by evaporation with ethanol.

The present invention provides methods of screening for a nucleoside analog that is incorporated and extended at high efficiency by HIV RT and causes incorrect base pairing. Briefly, incorporation of a nucleoside analog in triphosphate form by HIV RT can be determined using native RNA templates that contain all four bases. The reaction mixture contains three of the complementary deoxynucleoside triphosphates, one of which is labeled with an isotope such as tritium or $\alpha$-$^{32}$P. The deoxynucleotide substrate that is omitted corresponds to the base that is modified in the analog. Any extensive incorporation of the labeled nucleotide depends on incorporation and extension of the analog by HIV RT. The ability of the analog to be incorporated into the newly synthesized DNA is directly compared to that of the corresponding native deoxynucleoside triphosphate as a function of substrate concentration. Incorporation of the analog is expressed as a percent of incorporation of the complementary deoxynucleotide. As used herein, incorporation and extension at high efficiency by HIV RT means equal to or greater than one percent of that achieved with the natural complementary deoxynucleotide triphosphate.

The ability of an analog to cause incorrect base pairing may be determined by testing the mutagenic potential of the analog. For example, the mutagenic potential of an analog can be tested by examining the frequency and spectrum of mutations produced by the incorporation of an analog into gapped DNA. Briefly, where the gapped DNA consists of a gap that spans part of the lacZ gene in M13mp2 DNA, mutations can be identified by reduced $\alpha$-complementation of $\beta$-galactosidase activity. Gapped DNA is prepared by the method of Kunkel (*Proc. Natl. Acad. Sci. USA* 81:1494–1498, 1984) as modified by Feig and Loeb (*Biochem.* 32:4466–4473, 1993). The template is M13mp2 containing uracil and the gap is opposite the target sequence of 361 nucleotides spanning the lacZ regulatory region and the 145 5' bases of coding sequence. Incorporation is carried out using HIV RT with three complementary deoxynucleoside triphosphates and the designated deoxynucleoside triphosphate analog. If necessary, further extension is carried out with *E. coli* DNA polymerase and with the addition of the missing complementary deoxynucleoside triphosphate. The double-stranded DNA product is transfected into MC1061 cells. The uracil containing strand is rapidly hydrolyzed by uracil glycosylase and apurinic endonucleases and the resultant phage are made in vivo from the template strand that contains the analog. Mutant phage plaques are light blue or colorless after incubation with IPTG. The types of mutations produced can be determined by isolation of the phage DNA and sequencing the nucleotide segment that corresponds to the gap using a 15-mer oligonucleotide primer complementary to the +179 to +194 segment of the lacZα coding sequence by the method of Sanger (*J. Mol. Biol.* 125:225–246, 1978). In order for the nucleoside analog to be effective in the treatment of AIDS, it is necessary that it be mutagenic in the in vitro assays. The frequency of misincorporation per nucleotide residue incorporated in the in vitro assay should be three-fold or more greater than the observed using an equal amount of the corresponding complementary deoxynucleoside triphosphate.

The screening methods of the present invention may be used with a single analog or a mixture containing two or more analogs. Where it is desired to screen a mixture for the presence of analogs possessing the appropriate incorporation/extension and mutagenic properties, the mixture or portion thereof is typically tested for incorporation by HIV RT. The purification of analogs in a mixture can be monitored, for example, by measuring incorporation into gapped DNA as described above. Purification techniques are well known to those in the art and include chromatography, such as HPLC using ion exchange resins or reverse-phase columns. Once an analog is purified, it may be desirable to identify the chemical structures. An approach to the determination of a chemical structure is to use a combination of HPLC, UV spectroscopy, and mass spectrometry (e.g., Wood et al., *Biochem.* 29:7024–7032, 1990). For mass spectrometry, a sample can be separated from inorganic salts (e.g., by reverse-phase HPLC), converted to the triethylammonium salt, hydrolyzed in formic acid, converted to the trimethylsilyl derivative, and analyzed by gas chromatography/mass spectrometry using established methods (e.g., Dizdaroglu, *J. Chromatogr.* 295:103–121, 1984; Gajewski et al., *Biochem.* 29:7876–7882, 1990).

The methods of the present invention may be varied to screen for analogs having properties in addition to the ability to be incorporated and extended at high efficiency by HIV RT and to cause incorrect base pairing. For example, it may be desirable to screen for analogs that are also incorporated preferentially by HIV RT relative to incorporation by mammalian DNA polymerase and are not repaired by human DNA repair enzymes. Although a host genome has protection from an analog by cellular compartmentalization (i.e., HIV RT transcription occurs in the host cell cytoplasm which is isolated physically from the host DNA in the nucleus and in the mitochondria) and by DNA repair systems of the host, nevertheless, it may be desired to protect additionally by selecting for analogs that are incorporated preferentially by HIV RT versus mammalian DNA polymerase.

Incorporation of an analog by HIV RT and by mammalian DNA polymerase may be compared directly, or separately and the separate test results compared subsequently. Briefly, a comparison of incorporation of analogs among HIV RT and DNA polymerases can be carried out using a modification of the "minus" sequencing gel assay for nucleotide incorporation. A 5'-$^{32}$P-labeled primer is extended in a reaction containing three of the four deoxynucleoside triphosphates and an analog in the triphosphate form. The template can be either RNA or DNA. Elongation of the primer past the template nucleotide that is complementary to the nucleotide that is omitted from the reaction will depend and be proportional to the incorporation of the analog. The amount of incorporation of the analog is calculated as a function of the percent of oligonucleotide that is extended on the sequencing gel from one position to the next. Incorporation is determined by autoradiography followed by either densitometry or cutting out each of the bands and counting radioactivity by liquid scintillation spectroscopy. As used herein, preferential incorporation of an analog by HIV RT relative to incorporation by mammalian DNA polymerase means greater than two-fold over that achieved with any of the mammalian DNA polymerases using either an RNA or DNA template.

It will be evident to those in the art that the order in which the steps of the screening methods provided herein are performed may be readily varied. For example, the mutagenic potential of an analog may be tested prior to or subsequent to determining incorporation and extension by HIV RT.

The present invention, in another aspect, provides methods of treating an individual infected with HIV. Infected individuals are treated with a nucleoside analog that is incorporated and extended at high efficiency by HIV RT and causes incorrect base pairing. The analog may have additional properties, such as preferential incorporation by HIV RT relative to incorporation by mammalian DNA polymerase. With this aspect of the present invention, the nucleoside analogs are preferably in their unphosphorylated rather than their triphosphate forms. Unphosphorylated nucleoside analogs are able to more readily cross the membrane of a cell into its cytoplasm than the corresponding triphosphate forms. Once in the cytoplasm of a cell, an unphosphorylated analog is converted to the triphosphate form by endogenous kinases. The nucleoside analog in triphosphate form is then available for incorporation and extension by HIV RT.

An analog can be administered alone or in combination with other analogs or other therapeutic agents (e.g., chemo- or immunotherapeutic agents that work by other mechanisms). A variety of routes of administration may be used. Typically, administration will be by injection, orally or transdermally. Where another analog and/or therapeutic agent is used, administration can be simultaneous or sequential. The precise optimum dose for a particular analog may vary depending upon the analog and the patient. Generally, however, a therapeutically effective amount of an analog will be from about 0.1 mg to about 1 g per kg body weight. It will be evident to those in the art how to determine the optimal effective doses for a particular analog, and that the number and frequency of administration will be dependent upon the response of the patient. An analog is generally formulated in a pharmaceutically acceptable form for administration, and it will be evident to those in the art that the form may depend on the physical-chemical properties of the analog and its route of adsorption or absorption into the bloodstream. Suitable carriers or diluents include physiological saline for injection.

The following examples are offered by way of illustration and not by way of limitation.

EXAMPLES

Example I

Preparation of Nucleoside Analogs

A. 8-Hydroxydeoxyguanosine

8-Hydroxydeoxyguanosine (also known as 7,8-dihydro-8-oxodeoxyguanosine or 8-oxodeoxyguanosine) is synthesized according to a combination of the published procedures of Bodepudi et al. (*Chem. Res. Tox.* 5:608–617, 1992, and Lin et al. (*J. Med. Chem.* 28:1194–1198, 1985). As described by Bodepudi et al., to a cooled (0° C.) solution of 2'-deoxyguanosine (5.0 g, 19.0 mmol, available from Sigma Chemical Company, St. Louis, Mo.) in 30 mL of water, a saturated solution (120 mL) of bromine-water is added dropwise until the suspension becomes opaque and a yellow color persists. The precipitated 8-bromodeoxyguanosine is removed by filtration and washed with cold water followed by acetone. The solid is then recrystallized from methanol-water containing sodium bicarbonate to yield 8-hydroxydeoxyguanosine.

Two hundred mL of dimethyl sulfoxide (DMSO) are added to a freshly prepared solution of sodium benzoylate (made from benzyl alcohol (75 mL) and sodium (2.14 g)) under an atmosphere of argon. 8-Bromodeoxyguanosine (10 g, 29 mmol) in DMSO (80 mL) is added to the resulting mixture and the reaction is heated to 65° C. for 24 hours. After cooling to room temperature, the reaction mixture is neutralized with glacial acetic acid and the DMSO is removed by vacuum distillation at 65° C. The remaining solution is poured into ether with stirring. The oily residue that remains after decanting off the ether is added to acetone and the resulting white precipitate is removed by filtration. After stirring with water, the slurry is filtered and the collected white solid recrystallized from methanol to give 8-(benzyloxy)-2'-deoxyguanosine.

The final stage of the synthesis is accomplished according to the published procedure of Lin et al. (*J. Med. Chem.* 28:1194–1198, 1985). A solution of 8-(benzyloxy)-2'-deoxyguanosine (0.20 g, 0.54 mmol) in a mixture of methanol (8 mL) and water (8 mL) is hydrogenated over 10% palladium on carbon (0.3 g) at 50 psi and room temperature for 18 hours. The catalyst is removed from filtration and the solvent evaporated to dryness to yield 8-hydroxydeoxyguanosine.

B. $O^6$-Methyldeoxyguanosine, $O^6$-Ethyldeoxyguanosine and $O^6$-Isopropyldeoxyguanosine $O^6$-Methyldeoxyguanosine, $O^6$-ethyldeoxyguanosine and $O^6$-isopropyldeoxyguanosine are synthesized according to the published procedure of Fathi et al. (*Tetrahedron Lett.* 31:319–322, 1990). Trifluoroacetic anyhydride (2.3 mL, 16 mmol) is added to a cooled (0° C.) solution of 2'-deoxyguanosine (2 mmol, available from Sigma Chemical Company) in pyridine (10 mL). After 10 minutes, the appropriate alkoxide (4.3 g) in 300 mL of the appropriate alcohol (sodium methoxide in methanol for $O^6$-methyldeoxyguanosine, sodium ethoxide in ethanol for $O^6$-ethyldeoxyguanosine, sodium isopropoxide in isopropyl alcohol for $O^6$-isopropyldeoxyguanosine) is added dropwise and the reaction mixture is stirred for 24 hours (or 60 hours for the ethyl derivative and two days for the isopropyl derivative). The reaction is quenched with a solution of pyridinium hydrochloride (made from 12 mL pyridine and 4 mL of hydrochloric acid) and the excess acid destroyed with sodium bicarbonate (2 g). The mixture is then evaporated to dryness, resuspended in water and purified on a DYNAMAX (Rainin Instrument Co.) reversed-phase HPLC column using a gradient of 2–5% acetontrile in water over 45 minutes to yield $O^6$-methyldeoxyguanosine, $O^6$-ethyldeoxyguanosine or $O^6$-isopropyledeoxyguanosine, depending upon the particular alkoxide used above.

C. 5-Hydroxymethyldeoxycytidine

5-Hydroxymethyldeoxycytidine is synthesized according to the published procedure of Itahara et al. (*Chem. Lett.* 1591–1594, 1991). To 5-methyl-2'-deoxycytidine (0.5 mmol, available from Sigma Chemical Company) in 100 mL of sodium phosphate buffer (pH 7.0) $Na_sS_2O_8$ (0.5 mmol) is added and the reaction mixture stirred at 75° C. for 4 hours under argon. The reaction mixture is then concentrated and the crude 5-hydroxymethyldeoxycytidine is purified on a LiChroprep reversed-phase HPLC column by eluting with 0.05 M sodium phosphate (pH 7.0) and evaporation of the appropriate fractions.

D. $O^4$-Methylthymidine, $O^4$-Ethylthymidine and $O^4$-Isopropylthymidine $O^4$-Methylthymidine, $O^4$-ethylthymidine and $O^4$-isopropylthymidine are synthesized according to the published procedure of Xu et al. (*Nucleic Acids Res.* 18:4061–4065, 1990). t-Butyldimethylsilyl chloride is added to a solution of thymidine (12.1 g, 50 mmol, purchased from Sigma Chemical Company), imidazole (10.2 g, 150 mmol), and dimethylformamide (100 mL) at room temperature. After 3 hours, the solution is concentrated and the residue is dissolved in ether and washed twice with saturated aqueous sodium chloride. The organic layer is separated, dried ($Na_2SO_4$) and evaporated to yield 3',5'-O-di-t-butyldimethylsilylthymidine.

To a cooled (0° C.) suspension of 1,2,4-triazole (25.6 g, 370 mmol) in anhydrous acetonitrile (300 mL, $CH_3CN$), phosphoryl chloride (3 mL) is added followed by triethylamine (60 mL). After 1 hour, 3',5'-O-di-t-butyldimethylsilylthymidine (11.75 g, 25 mmol) in 100 mL of $CH_3CN$ is added over 30 minutes and the solution is stirred for 16 hours. The reaction mixture is then filtered, diluted with ethyl acetate and washed with sodium bicarbonate. The organic layer is dried ($Na_2SO_4$), filtered and the solvent evaporated to yield 3',5'-O-t-butyldimethylsilyl-4-(1,2,4-triazolo)thymidine.

To a cooled (0° C.) solution of 3',5═-O-t-butyldimethylsilyl-4-(1,2,4-triazolo)thymidine (5.11 g, 10 mmol) in 40 mL of dimethylformamide is added 3 mL of the appropriate alcohol (methanol, ethanol or isopropanol) and 1,8-diazabicyclo[5.4.0]undec-7-ene (2.5 mL). The solution is allowed to warm to room temperature then stirred for 3 additional hours for methanol or overnight for ethanol or isopropanol. After neutralization of the solution with $KH_2PO_4$, the product is extracted into chloroform, washed with saturated NaCl, dried over $Na_2SO_4$, and filtered. The filtrate is concentrated and the residue treated with tetrabutylammonium fluoride in tetrahydrofuran. The reaction is complete in 1 hr, and the reaction mixture is purified by column chromatography on silica gel, eluting with 2% methanol in chloroform. After evaporation of the appropriate fractions, the desired product ($O^4$-methylthymidine, $O^4$-ethylthymidine or $O^4$-isopropylthymidine, depending upon the particular alcohol reacted above) is then recrystallized from 5% methanol in ethylacetate.

E. $O^4$-Isobutylthymidine $O^4$-Isobutylthymidine is synthesized in a similar manner to the published procedure of Xu et al. (*Nucelic Acids Res.* 18:4061–4065, 1990) starting from 3',5'-O-t-butyldimethylsilyl-4-(1,2,4-triazolo)thymidine as described in section D above. To a cooled (0° C.) solution of 3',5'-O-t-butyldimethylsilyl-4-(1,2,4-triazolo)thymidine (5.11 g, 10 mmol) in dimethylformamide (40 mL) is added isobutyl alcohol (3 mL) and 1,8-diazabicyclo[5.4.0]undec-7-ene (2.5 mL). The solution is allowed to warm to room temperature then stirred until the reaction is complete. After neutralization of the solution with $KH_2PO_4$, the product is extracted into chloroform, washed with saturated NaCl, dried over $Na_2SO_4$, and filtered. The filtrate is concentrated and the residue is treated with tetrabutylammonium fluoride in tetrahydrofuran. The reaction is complete in about 1 hour and, after purification by column chromatography on silica gel, yields the desired $O^4$-isobutylthymidine.

F. 3,$N^4$-Ethenodeoxycytidine

3,$N^4$-Ethenodeoxycytidine is synthesized according to the published procedure of Eberle et al. (*Carcinogenesis* 10:2751–2756, 1989). To 2'-deoxycytidine (8 mg, available from Sigma Chemical Company) in 0.4 mL of DMSO is added 0.04 mL of a 45% aqueous solution of chloroacetaldehyde and the reaction mixture is stirred for 1 hour at 70° C. The reaction mixture is then evaporated to dryness and the resulting residue purified by reverse-phase HPLC on a Nucleosil C18 column (Altech) to yield 3,$N^4$-ethenodeoxycytidine.

G. 3,$N^2$-Ethenodeoxyguanosine

3,$N^2$-Ethenodeoxyguanosine is synthesized according to the published procedure of Kusmierek et al. (*Chem. Res. Tox.* 5:634–638, 1992). To a suspension of 2'-deoxyguanosine (0.3 g, 1.5 mmol, available from Sigma Chemical Company) and potassium carbonate (0.21 g, 1.5 mmol) in 5 mL of DMF is added 0.25 mL of a 45% aqueous solution of chloroacetaldehyde. After 12 hours the reaction mixture is diluted with water and purified on a Dowex 1×2 (200/400, in $HCO_3$ form) ion exchange column, eluting with a 2 liter linear gradient of 0–0.5 M $NH_4HCO_3$ in 50% aqueous methanol. Evaporation of the appropriate fractions gives 3,$N^2$-ethenodeoxyguanosine.

H. 1,$N^6$-Ethenodeoxyadenosine

1,$N^6$-Ethenodeoxyadenosine is available from Sigma Chemical Company.

I. 8-Aminodeoxyguanosine

8-Aminodeoxyguanosine is synthesized according to the published procedure of Long et al. (*J. Org. Chem.* 32:2751–2756, 1967). To a cooled (0° C.) solution of 2'-deoxyguanosine (5.0 g, available from Sigma Chemical Company) in 25 mL of water, a saturated solution of bromine-water is added dropwise until the suspension becomes opaque and a yellow color persists. The precipitated 8-bromodeoxyguanosine is removed by filtration and washed with cold water followed by acetone. The solid is then recrystallized from methanol-water containing sodium bicarbonate to yield 8-bromodeoxyguanosine.

Hydrazine is added to a suspension of 8-bromodeoxyguanosine in water:methanol (150 mL; 1:2) and the resulting solution is heated at reflux for 24 hours. The resulting precipitate is removed by filtration and the filtrate is evaporated to a solid. After repeated evaporations from ethanol, the product is recrystallized from methanol. The purified 8-azido-2'-deoxyguanosine (1.3 g) is dissolved in a mixture of methanol:water (160 mL, 5:3), Raney nickel (10.0 g) is added, and the mixture is heated at reflux for 18 hours. The catalyst is removed by filtration through celite and after washing with water and methanol the filtrate is evaporated to dryness. The resulting solid is recrystallized from methanol to yield 8-aminodeoxyguanosine.

J. 5-Hydroxydeoxycytidine

5-Hydroxydeoxycytidine is synthesized in a similar manner to the published procedure of Eaton et al. (*Biochem. Biophys. Acta* 319:281–287, 1973) for 5-hydroxydeoxycytidine-3',5'-diphosphate. Bromine is added to a cooled (0° C.) solution of 2'-deoxycytidine (available from Sigma Chemical Company) in water until the yellow color persists. The excess bromine is quenched with cyclohexene and 2,4,6-collidine is added. After 2 hours, the reaction mixture is washed with ether and evaporated to dryness under vacuum. The crude 5-hydroxydeoxycytidine is then purified by reversed-phase HPLC on an ULTRASPHERE C18 column (Phenomenex) using a linear gradient of 0%–20% B in A (solvent A: 0.1 M $NH_4OAc$, solvent B: 50% $CH_3CN$ in 0.1 M $NH_4OAc$).

K. 5,6-Dihydro-5,6-dihydroxydeoxycytidine (Cytidine glycol)

The deoxynucleoside cytidine glycol is synthesized based upon the published procedure of Basu et al. (*Proc. Natl. Acad. Sci.* 86:7677–7681, 1989) for the synthesis of thymidine glycol. To thymidine (available from Sigma Chemical Company) at 37° C. is added osmium tetroxide at pH 8.6. The solution is incubated for 10 minutes. Excess osmium tetroxide is extracted with ether and the crude reaction mixture purified by reverse-phase HPLC on an ULTRASPHERE C18 column using a linear gradient of 0%–20% B in A (solvent A: 0.1 M $NH_4OAc$, solvent B: 50% $CH_3CN$ in 0.1 M $NH_4OAc$).

Example II

Screening for Nucleoside Analogs that are Incorporated and Extended by HIV RT and Cause Incorrect Base Pairing A. Testing a Mixture of Analogs for Incorporation by HIV RT The purification of oxidized derivatives of dCTP is monitored by measuring incorporation into gapped DNA. The gapped DNA consists of a single-stranded circular M13mp2 DNA containing uracil residues annealed to a linear incomplete complementary strand lacking uracil so as to create a 361-nt gap spanning part of the lacZ gene (prepared as described in Feig and Loeb, *Biochemistry* 32:4466–73, 1993). The reaction mixture (0.02 ml) contains: 200 ng of gapped DNA, 60 mM Tris-HCl (pH 8.0), 10 mM KCl, 7 mM $MgCl_2$, 1 mM dithiothreitol, 0.5 mM EDTA, 200 μM (each) dATP, dGTP and TTP, 1 μM [α-$^{32}$P]dCTP or modified dCTP (692 cpm/pmol), and 1.25 units of recombinant HIV-RT (Preston et al., *Science* 242:1168–1171, 1988) (1 unit is the amount of enzyme required to catalyze the incorporation of 1 nmol of dNTP into DNA in 1 h at 37° C.). The nucleotide bias in this reaction drives the incorporation of modified cytosine only at sites opposite guanosines in the lacZα gene. Samples are extracted once each with phenol and chloroform/isoamyl alcohol, 24:1, followed by ethanol precipitation in the presence of 400 mM NaCl and 10 μg of glycogen (as a coprecipitant). Samples are resuspended in $H_2O$, and gap-filling synthesis is completed with *E. coli* DNA polymerase I, large fragment (pol-1lf) in 20 μl reactions containing the DNA from a reaction with HIV-RT, 50 mM Tris pH 7.8, 10 mM $MgCl_2$, 200 μM (each dATP, dCTP, dGTP and TTP, and 5 units of pol-1lf. Reactions are incubated at 37° C. for 45 minutes and stopped by the addition of 80 μl of 25 mM EDTA and incorporation into an acid insoluble precipitate is determined (Feig and Loeb, *Biochemistry* 32, 4466–73, 1993).

B. Creating and Purifying a Mixture of dCTP Analogs

Oxidation of dCTP is carried out in a 200 μl reaction containing: 5.4 mM [α-$^{32}$P]dCTP (692 cpm/pmole dCTP), 10 mM Tris-HCl (pH 7.5), 750 μM $FeSO_4$, 15 mM $H_2O_2$, and 1.5 mM ascorbic acid. Samples are incubated in 1.7 ml tubes at 37° C. for 40 min. Reactions are stopped by the addition of 5 μl of 100 mM deferoxamine (chelating agent), and the mixture is immediately loaded onto a Beckman ODS, reverse phase HPLC column (4.6×250 mm), equilibrated with 50 mM triethylammonium acetate, pH 7.0. Nucleotides are eluted with 15 ml of triethylammonium acetate followed by a linear 45-ml gradient from 0%–25% acetonitrile at a constant flow rate of 1 ml/min. Sixty 1-ml fractions are collected and screened for UV absorbance at 254 nm (measured by HPLC UV absorbance detector), for radioactivity and for incorporation into gapped DNA by HIV reverse transcriptase. Fractions that are most efficiently incorporated into DNA and are well separated from undamaged dCTP are pooled and lyophilized. The lyophilized fractions from the $C_{18}$ column are resuspended in 125 mM $KH_2PO_4$/125 mM KCl pH 4.4 and loaded onto a Whatman PARTISIL 10 SAX HPLC column (4.6×250 mm) which is equilibrated in 125 mM $KH_2PO_4$/125 mM KCl pH 4.4. An isocratic mobile phase of 125 mM $KH_2PO_4$/125 mM KCl pH 4.4 is run at a flow rate of 2 ml/min. One hundred fifty, 1-ml fractions are collected and screened for radioactivity and incorporation into gapped DNA.

The column fractions are used in place of dCTP for DNA synthesis reactions. The DNA template is a double-stranded M13mp2 molecule with a 361-nt single-stranded gap spanning part of the lacZ gene for bacterial β-galactosidase. The uracil-containing strand is rapidly hydrolyzed upon transfection in *E. coli*, resulting in a $10^4$-fold preferential expression of the strand lacking uracil and preventing the repair of altered cytidines incorporated into the strand lacking uracil. DNA synthesis is catalyzed by HIV RT in the presence of 200 μM dATP, dGTP and TTP and 1 μM of each fraction from the reverse-phase column. Partially double-stranded DNA products are purified, and gap filling synthesis is completed using the Klenow fragment of *E. coli* DNA polymerase I. Incorporation of oxidized cytosine derivatives is quantified by scintillation counting and the toxicity of the fractions is assessed by comparing the transfection efficiency of DNA synthesized by using fractions containing the altered nucleotides to that of DNA synthesized with dCTP passed through the same column. The mutagenicity of each fraction is measured by scoring forward mutations in the lacZ gene for β-galactosidase (Kunkel, *Proc. Natl. Acad. Sci. USA* 81:1494–1498, 1984).

With the reverse-phase column, not all of the $^{32}P$-containing species are incorporated into DNA, presumably because they are no longer a substrate for HIV-RT. dCTP and dUTP elute from the reverse-phase column in fractions 29–31 and 34–35, respectively. Fractions 12–14 are highly mutagenic and lack undamaged nucleotides. Fractions 12–14 are combined, loaded onto a strong anion exchange (SAX) column, and six species, α, β, γ, δ, ε, ζ, separated. Compounds γ and ε are incorporated into DNA by HIV-RT with efficiencies of about 56% and 27% of that for dCTP. Neither species is incorporated appreciably by mammalian DNA polymerase-α, and only γ is a substrate for mammalian DNA polymerase-β (18% relative to dCTP).

Fractions from successive steps in the purification of γ were analyzed by TLC. Oxidative damage to cytidine can result in >40 modified nucleotide species. The reverse-phase step separates γ species from most of the other products, and the strong anion-exchange column further purified it.

C. Testing Mutagenic Potential

Mutations produced by the incorporation of oxidized derivatives of dCTP into gapped DNA are identified by reduced α-complementation of β-galactosidase activity. Logarithmic-phase MC1061 [hsdR, mcrR, araD, (139Δ⁻ araABC⁻leu) 7679ΔlacX74, galU, galK, rspL, thi⁻] is prepared for electroporation by washing the cells four times with sterile $H_2O$. Cells are then pelleted and resuspended in a volume of $H_2O$ equal to that of the packed cells. Fifty nanograms of the filled-gap DNA product is mixed with 300 μl of cells and subjected to electroporation using a Bio-Rad Gene Pulser (25 mF, 400 W, 2.0 KV, and time constants between 6.0 and 7.5). Samples are placed on ice and mixed with 1 ml of LB medium. Aliquots (10–40 μl) of the transfection mixtures are added to 3 ml of molten top agar (42° C.) consisting of 0.9% NaCl, 0.8% Bacto Agar, 0.08% 5-bromo-4-chloro-3-indolyl β-D-galactoside dissolved in dimethylformamide, and 0.2 ml of CSH50 [Δ(proBlac)/F'+ raD36, thi⁻, ara⁻, proAB, lacI$^{α}$Z⁻Δm15] cells in logarithmic phase, and layered onto plates containing 30 ml of solidified M9 medium supplemented with 1.5% Bacto Agar and 15 mM isopropyl-β-D-thiogalactoside (IPTG). Phenotypes are confirmed by mixing mutant phage with an equal quantity of wold type M13mp2 phage and replating. Phage DNA is isolated (Kunkel, *Proc. Natl. Sci. USA* 81:1494–1498, 1984) and sequenced by the method of Sanger et al. (*J. Mol. Biol.* 125:225–246, 1978) using a 15-mer oligodeoxyribonucleotide primer complementary to the +179 to +194 segment of the lacZα coding sequence.

Mutagenic potential of γ is assessed by using a forward mutation assay. To reduce the frequency of mutations arising from the incorporation of noncomplementary nucleotides by HIV-RT, this incubation is performed for only 2 min. Under these conditions, HIV-RT incorporates approximately five molecules of γ or nine molecules of undamaged dCTP per molecule of template. The gapped DNA is them completely filled by pol-IIf (the large fragment of *E. coli* DNA polymerase I) using the four undamaged nucleotides as substrates. The transfection efficiencies and mutation frequencies are given in Table I. In reactions without HIV-RT, 1040 transfectants are obtained per ng DNA, whereas with HIV-RT and undamaged dCTP ("purified" by reverse-phase and strong-anion exchange chromatography) the yield is 165 transfectants per ng of DNA. Substitution of γ for dCTP further reduced transfection efficiency, 73 transfectants per ng of DNA. In the absence of HIV-RT the mutation frequency is $4.6 \times 10^{-4}$ (line 1, Table I). The reaction with HIV-RT and dCTP increases mutation frequency 2.4-fold, presumably from the high frequency of misincorporation by HIV-RT and the nucleotide pool bias in the reaction mixture. Most importantly, the mutation frequency secondary to the incorporation of an average of five molecules of γ per template DNA is $1200 \times 10^{-4}$, an increase of 109-fold. The relatively low mutation frequency in the control reaction with only 3 nt (line 4, Table I) indicates that the mutagenesis induced by γ does not result from the lack of dCTP in the mixture.

TABLE I

MUTAGENESIS BY γ

| HIV-RT | Cytosine substrate for HIV-RT | Transfection efficiency, plaques per ng | Mutation frequency |
|---|---|---|---|
| − | — | 1040 | $4.6 \times 10^{-4}$(41) |
| + | — | 183 | $31 \times 10^{-4}$(91) |
| + | dCTP | 165 | $11 \times 10^{-4}$(54) |
| + | γ | 73 | $1200 \times 10^{-4}$(196) |

HIV-RT is used to incorporate dATP, dGTP, and dTTP alone, with dCTP, or with γ, as shown in column 2. Transfection efficiencies and mutation efficiencies are shown in columns 3 and 4. Number of mutants isolated for each class of reactions appear in parentheses. Data is cumulative for several experiments.

The mutation spectrum resulting from the incorporation of γ into the lacZ target gene is prepared based upon the sequencing of about 200 nt within the gap in each of 92 of the 196 mutants isolated. Of the 181 observed substitutions, 178 (98.3%) occur at cytosines (opposite guanines in the template strand of the gapped DNA). This result indicates that despite the pool bias against dCTP, γ nearly invariably base-pairs with guanine during DNA synthesis by HIV-RT. Of the mutations, 173 (95.6%) were C→T transitions, showing the strong specificity of mutations caused by γ.

D. Structural Identification

The chemical structure of γ is determined to be 5-hydroxy-2'-deoxycytidine 5'-triphosphate by a combination of HPLC, UV spectroscopy, and mass spectrometry. γ is enzymatically dephosphorylated to the deoxynucleoside and analyzed by HPLC. Both the UV spectra (absorbance maximum of 292 nm) and the chromatographic retention time of the deoxynucleoside derived from γ are identical with an authentic sample of 5-hydroxy-2'-deoxycytidine. A fraction of γ is then separated from inorganic salts by reverse-phase HPLC, converted to the triethylammonium salt, hydrolyzed in formic acid, converted to the trimethylsilyl (TMS derivative), and analyzed by gas chromatography/MS using established methods (Dizdaroglu, *J. Chromatogr.* 295:103–121, 1984; Gajewski et al., *Biochemistry* 29:7876–7882, 1990). Both the chromatographic retention time and the mass spectrum of the γ derivative are consistent with the TMS derivative of 5-hydroxycytosine. The predominant ions in the mass spectrum of the TMS derivative of 5-hydroxycytosine derived from γ are m/z 343 (parent ion), m/z 342 [M–H]$^+$ and m/z 328 [M–CH$_3$]$^+$, consistent with published data. The UV spectrum of γ, however, clearly shows that the base moiety was 5-hydroxycytosine and not cytosine glycol prior to acid hydrolysis.

E. Comparing Incorporation of purified deoxynucleoside triphosphate analogs by HIV RT versus by mammalian DNA polymerases 1. Determining incorporation by HIV RT Incorporation of nucleoside triphosphates by HIV RT or any reverse transcriptase is usually determined by measuring the initial rate of incorporation of a labeled deoxyribonucleoside triphosphate into an acid insoluble product with a polyribonucleotide template (Hahn et al., *Science* 232L:1548, 1986). An example of such as assay is the use of poly rC oligo dG as a template and [α-$^{32}$P]dGTP as the radiolabeled substrate. Although this is the easiest method to quantitate the activity of HIV RT and is described herein to assess the production of virus during serial passage of infected cells in culture, it is inadequate for assessing the incorporation of nucleoside analogs in their triphosphate form.

For measurements of the incorporation of nucleoside analogs, native RNA templates that contain all four bases are used. Firstly, these templates mimic the template used by the HIV RT in vivo for first strand cDNA synthesis. Secondly, polyribonucleotides that contain only one or two nucleotide species would be inadequate for chain extension assays since HIV RT slips during catalysis extensively with repetitive sequences (Roberts et al., *Molec. Cell Biol.* 9:469, 1989). Lastly, with homopolymers, one requires a different homopolymer to test each species of nucleotide analogs. In experiments with natural RNA templates, the reaction mixture contains three of the complementary deocynucleoside triphosphates, one of which is labeled with an isotope such as tritium or α-$^{32}$P. The deoxynucleotide substrate that is omitted corresponds to the base that is modified in the analog. Any extensive incorporation of the labeled nucleotide depends on incorporation and extension of the nucleoside analog in triphosphate form by HIV RT. For example, with the deoxynucleoside triphosphate derivative of 8-hydroxyguanine (8-oxo-dGTP) as a substrate, the reaction lacks dGTP; with 5-OH-dCTP, the omitted nucleotide is dCTP. A typical reaction mixture contains, in a total volume of 50 mL, the following: 60 mM Tris-HCl (pH 8.2), 1.0 mM dithiothreitol, 7 mM MgCl$_2$, 0.5 mM EDTA, 10 mM KCl, 50 µM of dCTP, dATP, 5.0 µM [α-$^{32}$P]dTTP (Specific radioactivity, 1000 to 10,000 cpm/pmol), an analog of dGTP, 20 units of HIV RT and 5 µg of a primed RNA template. Incubation is for 30 minutes at 37° C. and incorporation is determined after extensively washing the acid-insoluble product and counting by liquid scintillation (Battula and Loeb, *J. Biol. Chem.* 249:4086, 1974). The ability of the nucleoside analog in triphosphate form to be incorporated into the newly synthesized DNA is directly compared to that of the corresponding native deoxynucleoside triphosphate as a function of substrate concentration. Incorporation of the analog is expressed as a percent of incorporation of the complementary deoxynucleotide.

a. Preparation of RNA templates for incorporation and gel extension

Two different primed RNA templates are used in both the incorporation studies and in the analysis of the product by electrophoresis in polyacrylamide gels. The first contains an RNA that is complementary to a portion of the lacZα gene. By using a portion of the lacZ gene, the types and the frequencies of the nucleotide substitutions (mutations) that are produced as a result of copying by HIV RT are measured using the principle of alpha complementation (Kunkel, *J. Biol. Chem.* 260:5787, 1985). The RNA is transcribed by T3 RNA polymerase in vitro using the pBluescript SK+ plasmid (Stratagene) as previously described (Ji and Loeb, *Biochem.* 31:954, 1992). The transcription reaction in a volume of 50 µL contains: 40 mM Tris-HCl (pH 7.5), 6 mM MgCl$_2$, 2 mM spermidine, 10 mM NaCl, 10 mM dithiothreitol, 500 µM each of the four rNTPs, 3 ug of linearized pBluescript plasmid DNA, 30 units of T3 RNA polymerase and 2 units of RNasin. After incubation for 60 minutes at 37° C., the reaction product is digested with RNase-free DNAase and incubated for 60 min. The RNA is purified by extraction with phenol/chloroform and precipitated with ethanol. The primed RNA template is assembled by annealing a labeled primer consisting of the sequence (TTC GCT ATT ACG CCA GCT; SEQ ID NO: 1) as described (Williams et al., *J. Biol. Chem.* 265:18682, 1990).

An alternate template for measuring incorporation is a portion of the envelope protein of HIV-1 (env-V-1). The RNA template contains the nucleotide sequence complementary to regions 317–533 numbered from the envelope transcriptional initial site. The template is constructed by PCR amplification of a pBluescript KS$^+$-derived plasmid pME235 (Ji and Loeb, *Virology* 199:323, 1994) using oligodeoxynucleotides that are complementary to the envelop sequences 317–339 and 513–533 and each of which contains a T7 RNA polymerase binding sequence and the preferred transcription initiation site at the 5' terminus. The sequences of the oligonucleotides are as follows: Oligo I (ATT TTA ATA CGA CTC ACT ATA GGG ATA TAA TCA GTT TAT GGG ATC; SEQ ID NO: 2) and Olio II (AAT TTA ATA CGA CTC ACT ATA GGG ATA TTC TTT CTG CAC CTT ACC; SEQ ID NO: 3). The procedure for PCR amplification is well known to those skilled in the art (e.g., Sambrook et al., *Molecular Cloning: A Laboratory Manual,* 2 ed., Cold Spring Harbor Laboratory Press, 1989). The RNA envelop gene fragment for studies on incorporation of deoxynucleoside triphosphate analogs is synthesized using T7 RNA polymerase as detailed by Bio-Rad (Richmond, Calif.).

b. Determining incorporation by mammalian DNA polymerases

Five different mammalian DNA polymerases have been identified, purified and characterized. These are designated as DNA polymerases $\alpha$, $\beta$, $\gamma$, $\delta$, $\epsilon$ based on their amino acid sequences, intracellular localization and presumed role in cellular DNA metabolism (Fry and Loeb, CRC Press, 1986). The ability of a human DNA polymerase to incorporate a deoxynucleoside triphosphates analogs is determined using a DNA template that corresponds to the sequence of the RNA template used to analyze incorporation by HIV RT. A direct comparison is made on the incorporation of nucleoside analogs in the triphosphate form using a human DNA polymerase with that of HIV RT.

c. The assessment of DNA repair

It may be desirable to analyze DNA repair of nucleoside analogs following their insertion into the DNA strand of an RNA-DNA hybrid. This product arises from first strand synthesis by HIV RT. This hybrid is in the cytoplasm of infected cells and thus should not be available for repair by cellular glycosylases and nucleases. In order to quantitate the susceptibility of the nucleotide analogs to excision by cellular enzymes, oligonucleotides containing radiolabeled analogs at specified positions are synthesized based upon the protocols described herein. An oligoribonucleotide of 30 nucleotides in length is hybridized to a oligodeoxyribonucleotide primer of 15 nucleotides in length that is complementary to the first 15 nucleotides at the 3' template terminus. This leaves a stretch of 15 unpaired nucleotides that can be copied by a DNA polymerase or a viral reverse transcriptase. The primer is extended by a single addition step by incorporating a labeled deoxyribonucleoside triphosphate analog that is complementary to the first nucleotide downstream from the 3'-primer terminus (Zakour et al., Nucleic Acid Res. 12:6615, 1984). The extended primer is incubated with RNase and then purified by polyacrylamide gel electrophoresis and separated by salt extraction. Thereafter, the one nucleotide elongated primer is rehybridized to a fresh aliquot of the original oligoribonucleotide template and elongated by synthesis with HIV RT in the presence of all the complementary nucleoside triphosphates. The product of the reaction is purified by extraction with phenol/chloroform and precipitated with ethanol. To quantitate repair of the incorporated analog, the RNA-DNA hybrid, containing the nucleotide analog, is incubated with cytologic extracts obtained from human peripheral blood lymphocytes that were cultured in the presence of phytohemaglutinin for 3 days. The rate of removal of the analog is quantified by the amount of radioactivity rendered acid-soluble as a function of time of incubation. Control templates consist of a labeled non-adducted nucleotide at the same position. The same assay can be used for the analysis of removal of the adduct in different types of cells harboring HIV.

d. Comparing incorporation

A detailed comparison of incorporation of the nucleotide analogs among purified DNA polymerases and reverse transcriptases is carried out using a modification of the "minus" sequencing gel assay for nucleotide incorporation. A two fold molar excess of an oligodeoxyribonucleotide (20 mer) labeled with $^{32}P$ at the 3' terminus is hybridized to either an RNA or DNA oligonucleotide that contains the nucleotide sequence of a region of the HIV envelope gene (env-1). The synthesis of these oligonucleotide templates is detailed above. The resultant 5'-$^{32}P$-labeled primer is extended in a reaction containing three of the four deoxynucleoside triphosphates and the nucleoside triphosphate analog to be studied. The enzymes used for extension include each of the known eukaryotic DNA polymerases, reverse transcriptases from different RNA tumor viruses and HIV RT. HIV RT is purified as previously described (Preston et al., Science 242:1168, 1988; Ji and Loeb, Biochem. 31:954, 1992). In this assay, elongation of the primer past the template nucleotide that is complementary to the nucleotide that is omitted from the reaction will depend upon and be proportional to the incorporation of the nucleoside triphosphate analog.

As an example, the olignonucleotide template primer complex is incubated with HIV RT at 30° C. for 30 minutes a total volume of 10 $\mu$L containing 20 mM Tris-HCl (pH, 8), 25 mM KCl, 6 mM $MgCl_2$, 2 mM dithiothreitol, 0.1 mg/ml BSA, 50 $\mu$M dATP, dGTP, dATP, and 5-OH-dCTP and 1.0 units of HIV RT. The product of the reaction is isolated by chromatography of SEPHADEX G-100 (Pharmacia) and analyzed by electrophoresis through 15% polyacrylamide sequencing gels (Preston et al., J. Biol. Chem. 262:13821, 1987). The amount of incorporation of the nucleotide analog is calculated as a function of the percent of oligonucleotide that is extended on the sequencing gel from one position to that of the next. Incorporation is determined by autoradiography followed by either densitometry or cutting out each of the bands and counting radioactivity by liquid scintillation spectroscopy. This method provides a direct comparison of both incorporation and extension by different DNA polymerase and reverse transcriptases.

Example III

Testing for Nucleoside Analogs that are Lethally Mutagenic for HIV

This invention, in one aspect, provides compositions and methods for introducing mutations in HIV to a level that exceeds the capacity of the virus to propagate. In published protocols for the testing of nucleotide analogs that inhibit HIV RT, one tests nucleoside analogs that exhibit antiviral activity by the ability of the analogs to reverse the cytopathic effects of HIV infection (Pauweis et al., J. Virol. Methods 20:309, 1988; Baba et al., Proc. Natl. Acad. Sci. USA 88:2356, 1991; Busso et al., AIDS Res. Human Retroviruses, 4:449, 1988). This invention treats infected individual with nucleoside analogs that cause the progressive accumulation of errors in the viral genome. In order to monitor this accumulation of errors, the rate of production of infectious virus particles is analyzed as a function of serial passage in infected cells in the presence of the nucleoside analogs. The analogs analyzed correspond to the nucleoside triphosphates tested in the analysis of incorporation, chain extension, DNA repair and mutagenicity.

A. Production of HIV after infection of cultured cells

The rate of replication of viable HIV is determined in cultures of human peripheral blood lymphocytes. Human peripheral blood lymphocytes are obtained from normal donors and separated by FICOLL gradient fractionation. The purified cells are suspended in RPMI 1640 medium containing 20% fetal calf serum, antibiotics (Loeb et al., Proc. Natl. Acad. Sci. USA 61:827, 1968) and interleukin 2 (Baba, Proc. Natl. Acad. Sci. USA 88:2356, 1991) and then induced to replication by stimulation with phytohemaglutinin. After three days of incubations, an inoculum of HIV corresponding to 1 ng of p24 is added to $10^6$ HPBL in 1.0 ml of culture (Romero et al., Proc. Natl. Acad. Sci. USA 88:8806, 1991). The level of HIV replication is determined after 4 days in culture by analyzing the supernatant using a quantitative ELISA assay (antibody is available from National Institutes of Health, Rockville, Md.) of the capsid antigen, p24 (McQuade et al., Science 247:454, 1990) or by measuring reverse transcriptase activity (Battula et al, J. Biol. Chem. 250:8404, 1975; Resnick et al., J. Infect. Dis. 154:1027, 1986). The supernatant is serially transferred to fresh cultures every 4 to 10 days and the amount of virus is determined as a result of the concentration of the nucleoside analog and number of passages in culture. Virus yield and infectivity is expressed as a percentage of the control to that obtained by the addition of the nucleotide analog.

An alternative system is to propagate HIV in MT-4 cells (Harada et al., *Science* 229,563, 1985). In this system, virus production is determined in the supernatant by precipitation of the virus with polyethylene glycol (10%) and NaCl (0.1M) (Lardner et al., *Science* 243:1731, 1989). The viral pellets are solubilized in buffer containing 0.5% TRITON X-100, 0.5 mM KCl, 50 mM Tris-HCl (pH 7.5), 1 mM phenylmethylsulfonyl fluoride and 5 mM β-mercaptoethanol. The amount of virus is quantitated by the amount of HIV RT activity using poly rC. oligo dG as a template-primer. The production of infective virions in the supernatant is monitored by incubation of the supernate with DEAE DEXTRAN-treated target MT-2 for 1 hour at 37° C. in 96-well microtiter plates and monitoring each well for the formation of giant syncytia (Busso et al., *AIDS Res. & Human Retroviruses* 4:449, 1988).

B. Accumulation of mutations in the HIV RNA

In this invention, nucleoside analogs are chosen for the treatment of HIV infection based on there capacity to induce random mutations throughout the viral genome. The rate and types of mutations that are introduced are determined by sequencing portions of the HIV genome. Since the mutations are introduced randomly, it is first necessary to amplify and clone individual HIV RNA molecules prior to sequencing. HIV RNA is isolated from infected cells after serial passage which diminish the production of the virus as a function of the presence of the nucleoside analog. Isolated HIV RNA is then amplified using the polymerase chain reaction. In order to minimize the accumulation of errors by PCR, portions of the viral RNA are copied by murine leukemia virus reverse transcriptase and then the cDNA copy is amplified by T7 DNA polymerase. Fresh T7 DNA polymerase is added after each amplification step since the enzyme is not heat stable and is denatured by heating to 95° C. in the PCR reaction. For each sample, a minimum of ten clones each containing either a region of the envelope gene or the reverse transcriptase gene are sequenced. The frequency of nucleotide substitutions within each of the gene segments is determined as a function of the number of nucleotides sequenced. A comparison of the loss of HIV infectivity to the number of accumulated mutations is used to assess the potency of each of the nucleoside analogs.

From the foregoing, it will be evident that, although specific embodiments of the invention have been described herein for purposes of illustration, various modifications may be made without deviating from the spirit and scope of the invention.

We claim:

1. The compound $O^4$-isobutylthymidine.

2. A composition comprising the compound according to claim 1 in combination with a pharmaceutically acceptable carrier or diluent.

3. A method of treating an individual infected with human immunodeficiency virus (HIV), comprising administering a therapeutic amount of a nucleoside analog which does not terminate DNA synthesis upon incorporation by HIV reverse transcriptase, wherein said analog is incorporated and extended at high efficiency by HIV reverse transcriptase and wherein the incorporated analog causes incorrect base pairing.

4. The method of claim 3 wherein the nucleoside analog is 5-hydroxydeoxycytidine.

5. A method of treating an individual infected with human immunodeficiency virus (HIV), comprising administering a therapeutic amount of a nucleoside analog which does not terminate DNA synthesis upon incorporation by HIV reverse transcriptase, wherein said analog is extended at high efficiency and incorporated preferentially by HIV reverse transcriptase relative to mammalian DNA polymerase and wherein the incorporated analog causes incorrect base pairing.

6. The method of claim 5 wherein the nucleoside analog is 5-hydroxydeoxycytidine.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO:1:

TTCGCTATTA CGCCAGCT                                                18

(2) INFORMATION FOR SEQ ID NO:2:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (xi) SEQUENCE DESCRIPTION: SEQ ID NO:2:

ATTTTAATAC GACTCACTAT AGGGATATAA TCAGTTTATG GGATC                  45

(2) INFORMATION FOR SEQ ID NO:3:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (xi) SEQUENCE DESCRIPTION: SEQ ID NO:3:

AATTTAATAC GACTCACTTA TGGGATATTC TTTCTGCACC TTACC                  45